United States Patent [19]

Jonec

[11] Patent Number: 5,722,136
[45] Date of Patent: Mar. 3, 1998

[54] PAPER ROLL DISPENSABLE MALE URINARY AID AND METHOD OF MAKING SAME

[76] Inventor: Viliam Jonec, 19015 Rosita St., Tarzana, Calif. 91356

[21] Appl. No.: 344,437

[22] Filed: Nov. 23, 1994

Related U.S. Application Data

[63] Continuation-in-part of Ser. No. 216,906, Mar. 22, 1994.
[51] Int. Cl.[6] .................................................. A47K 11/12
[52] U.S. Cl. .......................... 4/144.4; 4/144.1; 4/144.2; 4/144.3; 428/43; 428/906; 604/326; 604/349
[58] Field of Search .................... 4/144.1, 144.2, 4/144.3, 144.4, 114.1, DIG. 5, 245.7, 245.8; 604/326, 329, 349; 428/43, 34.1, 34.2, 34.3, 36.9, 36.91, 906; 229/93, 4.5; 141/337, 331, 339

[56] References Cited

U.S. PATENT DOCUMENTS

| 2,855,607 | 10/1958 | Sullivan | 4/144.2 |
| 3,200,415 | 8/1965 | Breece, Jr. | 4/144.2 |
| 3,979,050 | 9/1976 | Cilia | 428/34.3 |
| 4,296,502 | 10/1981 | Bortle | 4/144.2 |
| 4,425,390 | 1/1984 | Changani et al. | 428/43 |
| 4,734,941 | 4/1988 | Dewitt et al. | 4/144.3 |
| 4,937,890 | 7/1990 | Tafur | 4/144.1 |
| 4,963,406 | 10/1990 | Gooding, Jr. et al. | 428/43 |

*Primary Examiner*—Henry J. Recla
*Assistant Examiner*—Charles R. Eloshway
*Attorney, Agent, or Firm*—John J. Posta, Jr.

[57] ABSTRACT

A convenient, disposable male urinary aid which allows a man to urinate directly into a toilet from a standing position by channeling the urine directly into water contained in the toilet bowl. A plurality of the urinary aids are formed as a roll of temporarily waterproof two-ply paper resembling conventional toilet paper, with the roll being divided into sheets by perforations. Multi-sheet segments are divided by double rows of perforations, with each multi-sheet segment forming one of the urinary aids with a channel comprising a passageway for liquid being formed between the two plies. Following use, the urinary aid may be flushed down the toilet, since it is made entirely of biodegradeable materials.

19 Claims, 2 Drawing Sheets

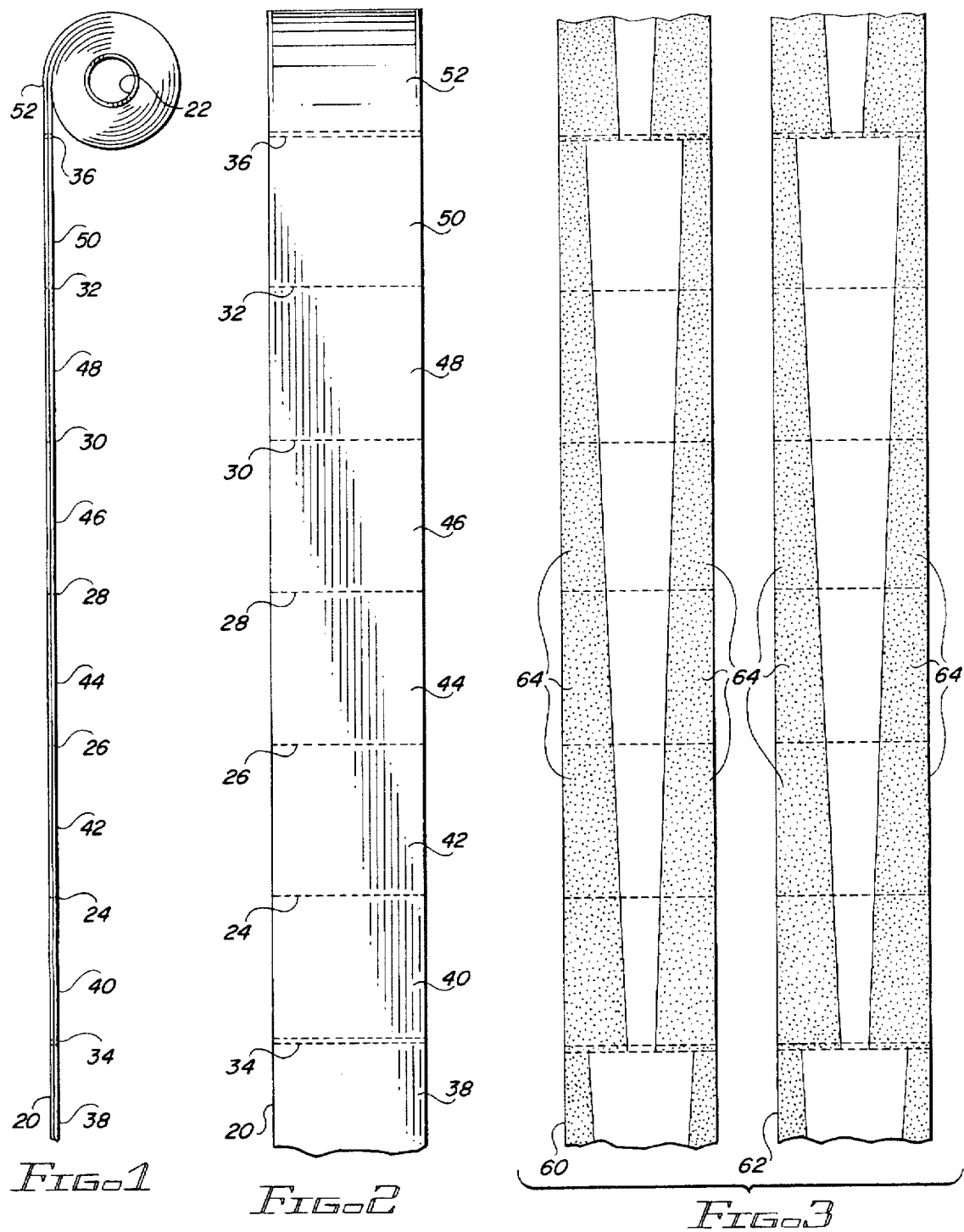

PAPER ROLL DISPENSABLE MALE URINARY AID AND METHOD OF MAKING SAME

This application is a continuation-in-part of U.S. patent application Ser. No. 08/216,906, filed on Mar. 22, 1994, and entitled "Flat-Folded Disposable Male Urinary Aid and Compact Portable Dispenser Therefor."

BACKGROUND OF THE INVENTION

Field of the Invention

The present invention relates generally to the field of male hygienic devices, and more particularly to a roll dispensable, disposable male urinary aid, a plurality of which disposable male urinary aids are contained in a continuous segment on a roll both resembling and useable as toilet paper, with each of the male urinary aids being useable to allow a man to urinate directly into a toilet from a standing position by channeling the urine through the male urinary aid directly into water contained in the toilet.

During the course of a normal day, most people will leave the comfort of their homes for a variety of reasons ranging from work, to shopping, to social events, and so forth. Such travel away from the home can range from a matter of hours to extended out-of-town trips which can last from days to weeks. With few exceptions, people will invariably find it necessary on a daily basis (or several times daily) to use toilet facilities which are outside their homes.

While toilet facilities exist in nearly every conceivable location in which people are likely to travel, the cleanliness of such facilities varies considerably. While some toilet facilities are maintained in spotless condition, others may be poorly or infrequently maintained, and may be filthy at best. Even the best of public facilities will quickly become unsanitary when used by individuals lacking proper toilet manners. Unfortunately, at times there simply is no choice but to use such unsanitary toilet facilities despite their unsanitary condition.

Women have been concerned about this problem for a long time, particularly since their anatomy makes it rather difficult to urinate from a standing position. The art has recognized this problem and has devised various solutions, including those taught in U.S. Pat. No. 2,690,658, to Willis; U.S. Pat. No. 4,023,216, to Li; U.S. Pat. No. 4,937,890, to Tafur; and U.S. Pat. No. 5,091,998, to Irazabal. The Li device and the Irazabal device are both rigid and are generally unsuitable for use outside of the home. However, the Willis device and the Tafur device are compact and disposable, and accordingly represent a solution accommodating the female anatomy to represent potential solutions to this problem for women.

Since men are able to urinate from a standing position, the problem is less severe for them than it is for women, particularly when using toilet facilities having urinals. When only a toilet is available, however, the same problem of unsanitary conditions also faces men, although to a lesser degree. While men can urinate into a toilet from a standing position, they are faced with the option of either lifting the toilet seat first, or engaging in socially unacceptable behavior and possibly urinating at least in part on the toilet seat. The toilet seat may be unsanitary and may carry germs, and thus lifting the seat may be unappealing, particularly if the last user did not lift the seat before urinating.

Another problem is that some men are uncomfortable with the noise generated by urinating into a toilet from a standing position, particularly when they are in a public toilet with others, rather than in a private toilet. In some cases, this difficulty can cause an inability to urinate until others have left the toilet. In addition, some men have difficulty aiming accurately—and are thus left with the choice of either cleaning up the toilet after urinating, or of leaving the toilet in a soiled condition.

The art has presented four potential solutions for men, the first three of which have accompanying problems of their own. The first three solutions are a modified toilet device having a urinal attachment, a wearable urinary appliance for storing urine which may be worn on the body, and a portable urinal. Examples of these three types of devices illustrate the fact that they do not represent a solution to the problems being discussed herein.

The first type of device is used to convert a conventional toilet into a urinal, and is illustrated by U.S. Pat. No. 3,412,408, to Michal, Jr.; U.S. Pat. No. 3,500,480, also to Michal, Jr.; U.S. Pat. No. 3,822,419, to Wilson, Sr.; and U.S. Pat. No. 4,985,940, to Jones. These devices are all more or less permanently attached to a toilet, and thus are certainly not portable. In addition, even if they were attached to a public toilet, most men would not use them due to the fact that their designs make them inherently unlikely to remain sanitary in a public toilet facility.

The second type of device is the wearable urinary appliance, and is illustrated by U.S. Pat. No. 1,490,793, to Ajamian, et al.; U.S. Pat. No. 2,840,079, to Conway et al.; U.S. Pat. No. 3,032,038, to Swinn; U.S. Pat. No. 3,306,296, to Moss et al.; U.S. Pat. No. 3,358,538, to Carrigan; U.S. Pat. No. 3,559,651, to Moss; U.S. Pat. No. 4,820,291, to Terauchi, et al.; and U.S. Pat. No. 4,846,816, to Manfredi. These devices all require the user to urinate into a container strapped to the body or a limb of the body and worn, and are more appropriate for incontinent men than for men who are not incontinent but rather merely faced with concerns about the sanitation of public toilet facilities.

The third type of device is a portable urinal, and is illustrated by U.S. Pat. No. 2,699,781, to Koch; U.S. Pat. No. 3,164,186, to Weber et al.; U.S. Pat. No. 3,403,410, to Benzel et al.; U.S. Pat. No. 3,432,865, to Schwartz; U.S. Pat. No. 4,294,582, to Naslund; and U.S. Pat. No. 5,235,705, to Belisle. These devices are simply not convenient, since they are not small enough to be carried (comfortably) by a man in his pocket, and since they present a disposal problem which is a greater problem than all of the aforementioned problems encountered when using public toilets.

The fourth type of apparatus, which largely overcomes the problems exemplified by the art described above, is a disposable male urinary aid as exemplified by U.S. patent application Ser. No. 08/216,906, filed on Mar. 22, 1994, which urinary aid was invented by the inventor of the present invention, is the parent of the present continuation-in-part application, and is hereby incorporated herein by reference. This urinary aid allows a man to urinate directly into a toilet from a standing position by channeling the urine directly into water contained in the toilet bowl. The urinary aid is made of temporarily waterproof paper, and is tapered from a larger diameter at the top end thereof, to a smaller diameter at the bottom end thereof. Following use, the urinary aid may be flushed down the toilet, since it is made entirely of biodegradeable materials.

This urinary aid is highly portable, and in fact a plurality of the urinary aids may be held in a dispenser in a folded, non-interleaved fashion, and dispensed therefrom when needed. The dispenser must be carried on the person of the user of the urinary aid, which does represent some degree of disadvantage. It would obviously be preferable for the urinary aids to be located in rest rooms, where they may be readily utilized.

The addition of yet another dispenser to a rest room is seen as an obstacle to location in the toilet stalls in rest rooms, since such dispensers would represent yet another device to be deployed and refilled in each toilet stall along with the toilet paper. This represents an additional cost which is likely to prevent the deployment of the urinary aids in public rest rooms. Accordingly, the predominant application of the urinary aids has continued to rest with the user of the urinary aids to this date.

It is accordingly the primary objective of the present invention that it present an improved urinary aid for facilitating urination by men from a standing position into a toilet, which improved urinary aid may be easily and conveniently dispensed in a rest room. It is a closely related objective that the urinary aid must be deployable in a rest room without the addition of any dispensers other than those which are currently present in virtually all rest rooms. It is an additional but also related objective of the present invention that it also provide a method for manufacturing the improved urinary aid of the present invention.

It is a related objective that the urinary aid of the present invention must act as a conduit for urine leading directly from the man's penis into the water of the toilet bowl to preclude a misdirected stream of urine, thereby ensuring both quiet urination and that the toilet seat will remain clean even when in its lowered position. It is an additional objective that the urinary aid of the present invention fit directly onto the penis, thereby compensating for those men who have difficulty in aiming accurately and directing urine into the water in the toilet bowl in an accurate manner. As such, it is an objective of the urinary aid of the present invention that it be temporarily waterproof while in use, but that it be disposable (and biodegradable) by dropping it into the toilet and flushing it following its use.

It is a further objective of the urinary aid of the present invention that it be convenient to use, and that it may be easily and quickly deployable in a rest room without requiring undue effort. In order to enhance the market appeal of the urinary aid of the present invention, it should be of inexpensive manufacture to thereby afford it the broadest possible market. Finally, it is also an objective that all of the aforesaid advantages and objectives of the improved urinary aid of the present invention be achieved without incurring any substantial relative disadvantage.

SUMMARY OF THE INVENTION

The disadvantages and limitations of the background art discussed above are overcome by the present invention. With this invention, a plurality of male urinary aids are contained in a roll of specially manufactured paper which may also be used as conventional toilet paper. In the preferred embodiment, the roll of paper is made of a continuous segment of two-ply temporarily waterproof paper wound onto a cardboard tube. The waterproof paper is perforated into a plurality of adjacent sheets, as is conventional. In the preferred embodiment, additional perforations are used to further separate adjacent multi-sheet segments of the roll, each of which multi-sheet segments forms one of the urinary aids.

The function of each multi-sheet segment urinary aid is to channel urine from the penis of a man into the water located in a toilet bowl. Each multi-sheet segment urinary aid has a channel formed between the two plies of waterproof paper by fastening the two plies together at the lateral edges of the multi-sheet segment, but not at a portion of the multi-sheet segment located intermediate the edges thereof. In the preferred embodiment, this channel formed between the two plies of waterproof paper is tapered from a larger diameter at the top end of the multi-sheet segment urinary aid, to a smaller diameter at the bottom end thereof.

Each of the two plies of waterproof paper used to form the roll of paper is made of thin, lightweight paper which is coated to be at least temporarily waterproof, yet which is sufficiently biodegradable to allow it to be flushed to dispose of the multi-sheet segment urinary aid once it has been used. Sufficient lengths of the two plies of waterproof paper are placed facing each other to form a long strip of two-ply paper. In a first embodiment, the two plies of waterproof paper are adhesively secured together with adhesive located between the plies (and adjacent the lateral sides of the two plies of waterproof paper).

In a second embodiment, the two plies of waterproof paper are mechanically secured together as is conventional in the art (with the mechanical connection being made adjacent the lateral sides of the two plies of waterproof paper). Thus, in either embodiment, each long strip of paper is formed from the two plies to create a continuous two-ply strip which contains a plurality of urinary aids.

Perforations are then placed along the length of the long strip of two-ply paper as mentioned above, both to form a series of sheets in the long strip of two-ply paper, and to form a series of multi-sheet urinary aids in the long strip of two-ply paper. In the preferred embodiment, a double row of perforations are used to separate adjacent multi-sheet urinary aids, while either a single row of perforations or the double row of perforations are used to separate adjacent sheets. The long strip of two-ply paper may then be wound onto a cardboard tube to form a roll, as is conventional.

It will at once be appreciated by those skilled in the art that the roll of paper may be used as conventional toilet paper, placed in a conventional dispenser in a rest room. In addition, by tearing off a single multi-sheet urinary aid along the double perforations, one urinary aid will be removed from the roll of paper. One end (the larger end if the channel in the multi-sheet urinary aid is tapered) is placed snugly over the end of the user's penis, and the other end of the multi-sheet urinary aid is placed into the water in a toilet bowl. When so placed, the water in the toilet bowl will tend to retain the end of the urinary aid when it is placed therein. The user may then urinate, and the urine will be funneled through the interior of the multi-sheet urinary aid, and into the toilet. When the user is done, he may remove the top end of the multi-sheet urinary aid from his penis, drop the multi-sheet urinary aid into the toilet, and flush it away.

It may therefore be seen that the present invention teaches an improved urinary aid for facilitating the urination by men from a standing position into a toilet, which improved urinary aid may be easily and conveniently dispensed in a rest room. The improved urinary aid is deployable from a paper roll located in the toilet paper dispenser of a rest room, thereby not requiring the addition of any dispensers in rest rooms. The paper roll thus functions both as conventional toilet paper, and as a urinary aid. A method for manufacturing the improved urinary aid of the present invention is also provided by the present invention.

The urinary aid of the present invention acts as a conduit for urine from the man's penis into the water of the toilet bowl to preclude a misdirected stream of urine, thereby ensuring both quiet urination and that the toilet will remain clean even when in its lowered position. The urinary aid of the present invention fits directly onto the penis, and thereby compensates for those men who otherwise have difficulty in aiming accurately and directing urine into the water in the toilet bowl in an accurate manner. The urinary aid of the present invention is temporarily waterproof while in use, but is disposable (and biodegradeable) and may be dropped into the toilet and flushed following its use.

The urinary aid of the present invention is convenient to use, and a roll containing a plurality of the urinary aids may be easily and quickly deployed in the toilet paper holder of a rest room without requiring undue effort. The urinary aids of the present invention are of inexpensive manufacture, thereby making them eminently affordable and providing them with the broadest possible market. Finally, all of the aforesaid advantages and objectives of the urinary aid of the present invention are achieved without incurring any substantial relative disadvantage.

DESCRIPTION OF THE DRAWINGS

These and other advantages of the present invention are best understood with reference to the drawings, in which:

FIG. 1 is a side view of a segment of a roll of two-ply paper wound on a cardboard tube, with a portion of the two-ply paper extending from the roll;

FIG. 2 is a front plan view of the roll of two-ply paper illustrated in FIG. 1, showing a plurality of perforations extending between the lateral sides of the portion of the two-ply paper extending from the roll, with single or double rows of perforations being used between adjacent sheets of the two-ply paper, with the double rows of perforations being used to separate adjacent multi-sheet urinary aids in the roll of two-ply paper;

FIG. 3 is a plan view of the portion of two-ply paper extending from the roll illustrated in FIGS. 1 and 2, with the two plies being separated from each other and with their facing sides being illustrated, showing where adhesive is located to form one of the urinary aids of the present invention in each multi-sheet segment of the two-ply paper, and also showing in the areas not to be adhesively secured together the definition of a longitudinal channel which will be located in each of the multi-sheet urinary aids;

DETAILED DESCRIPTION OF THE PREFERRED EMBODIMENT

Figure 4:
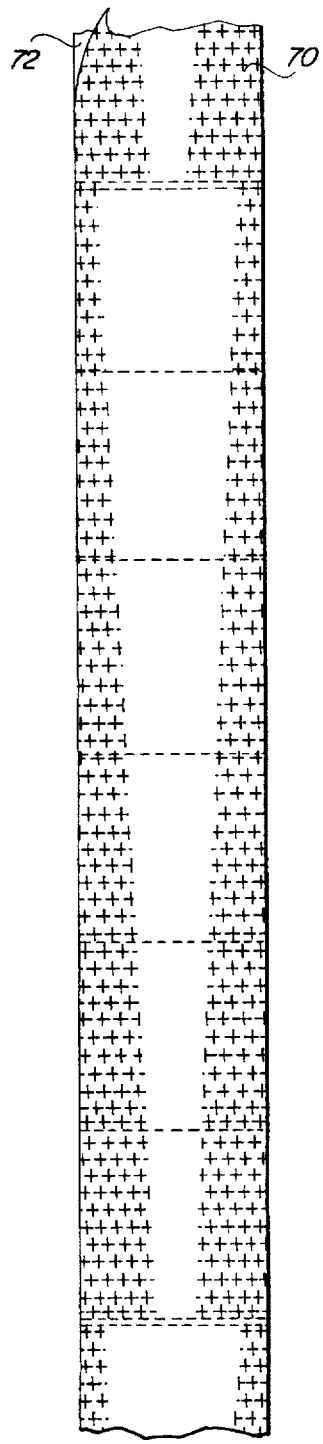
FIG. 4 is a plan view of a portion of two-ply paper similar to that illustrated in FIGS. 1 through 4, but with the two plies being held together through mechanical interlocking between the two plies, showing in the areas not mechanically secured together the definition of a longitudinal channel located in each of the multi-sheet urinary aids.

The preferred embodiment of the present invention uses a thin material which is temporarily waterproof, but which is ultimately biodegradeable when flushed down a toilet. One such material is coated paper, wherein the coating is water impermeable for at least a short period of time, but which will ultimately dissolve in water over a longer period of time. Thus, a thin grade of paper may be coated with this material to make it temporarily water impermeable, yet ultimately biodegradeable when flushed. In the preferred embodiment, the paper used is similar in weight to a tissue paper material, and it is coated with this material. Throughout the balance of this description of the present invention, this coated paper material will be referred to as waterproof paper.

Referring first to FIGS. 1 and 2, a long segment of waterproof paper 20 is illustrated which is wound onto a cylindrical cardboard tube 22. The long segment of waterproof paper 20 is of two-ply construction, as shown in FIG. 1. The manner of how the two plies are brought together will be discussed below in conjunction with FIGS. 3 and 4. As best shown in FIG. 2, a series of lateral perforations are located in the long segment of waterproof paper 20, with each series of perforations extending laterally from one side of the long segment of waterproof paper 20 to the other side thereof.

Some of the series of perforations are single rows of perforations 24, 26, 28, 30, and 32. Others of the series of perforations are double rows of perforations 34 and 36. Each series of perforations, whether single or double, is used to separate adjacent sheets of paper contained in the long segment of waterproof paper 20. Thus, the double row of perforations 34 separates two sheets of paper 38 and 40, the single row of perforations 24 separates two sheets of paper 40 and 42, the single row of perforations 26 separates two sheets of paper 42 and 44, the single row of perforations 28 separates two sheets of paper 44 and 46, the single row of perforations 30 separates two sheets of paper 46 and 48, the single row of perforations 32 separates two sheets of paper 48 and 50, and the double row of perforations 36 separates two sheets of paper 50 and 52.

It will thus be appreciated by those skilled in the art that in the conventional use of portions of the long segment of waterproof paper 20, as many sheets as desired may be torn off by using the single and/or double rows of perforations. The double rows of perforations such as 34 and 36 are used to separate multi-sheet segments of the long segment of waterproof paper 20. Thus, the double rows of perforations 34 and 36 are used to define a multi-sheet segment consisting of the sheets 40, 42, 44, 46, 48, and 50.

The double row of perforations 34 is used to separate the multi-sheet segment consisting of the sheets 40, 42, 44, 46, 48, and 50 from the preceding multi-sheet segment, which ends with the sheet 38. Similarly, the double row of perforations 36 is used to separate the multi-sheet segment consisting of the sheets 40, 42, 44, 46, 48, and 50 from the following multi-sheet segment, which begins with the sheet 52.

In the preferred embodiment, each of the multi-sheet segments in the long segment of waterproof paper 20 is six sheets long. Since the width of the long segment of waterproof paper 20 is approximately 4.5 inches (the width of a conventional roll of toilet paper), and since the sheets 40, 42, 44, 46, 48, and 50 in the following multi-sheet segment (as well as the rest of the sheets in the long segment of waterproof paper 20) are approximately square, the multi-sheet segment including the sheets 40, 42, 44, 46, 48, and 50 is approximately 27 inches long. Thus, each of the multi-sheet segments in the long segment of waterproof paper 20 are approximately 27 inches long.

Since the long segment of waterproof paper 20 is of two-ply construction, prior to placing the series of single and double perforations in the long segment of waterproof paper 20, it is necessary to conjoin the two plies together. This can be done in a variety of different ways. Two such manners of fabricating the two-ply construction will be discussed herein. The first of these fabrication techniques is accomplished by using an adhesive, and will be discussed in conjunction with FIG. 3, while the second fabrication technique is accomplished by using a mechanical interlocking to secure the two plies together, and will be discussed in conjunction with FIG. 4.

Referring first to FIG. 3, an adhesive technique for securing the two plies together is illustrated. In this technique, the long segment of waterproof paper 20 (FIGS. 1 and 2) consists of a long first ply of waterproof paper 60 and a long second ply of waterproof paper 62. In FIG. 3, the sides of the first and second plies of waterproof paper 60 and 62 which will face each other are shown. A channel will be defined between the first and second plies of waterproof paper 60 and 62 for each of the multi-sheet segments therein. This channel will not have adhesive therein, to thereby allow the channel between the first and second plies of waterproof paper 60 and 62 to act as a passageway for liquid.

The portions of the first and second plies of waterproof paper 60 and 62 along the lateral edges have adhesive material 64 placed thereon, and are illustrated as having a speckled appearance in FIG. 3. Note that the central spaces in each multi-sheet segment of the first and second plies of waterproof paper 60 and 62 are tapered in the preferred embodiment illustrated. Thus, the adhesive material 64 is placed along the lateral edges of the first and second plies of waterproof paper 60 and 62.

The adhesive material 64 is preferably a material which will be at least temporarily waterproof, but which will ultimately dissolve in water when flushed. The adhesive material 64 may be the same as the material used in coating the first and second plies of waterproof paper 60 and 62 which to make it temporarily waterproof.

The first ply of waterproof paper 60 is then folded over onto the second ply of waterproof paper 62 to form the long segment of waterproof paper 20. Note that the entire channel formed in each multi-sheet segment between the first and second plies of waterproof paper 60 and 62 will be unobstructed throughout its length. Following this assembly operation, the perforations will be placed in the long segment of waterproof paper 20, and the long segment of waterproof paper 20 will be wound onto the cardboard tube 22.

Referring now to FIG. 4, a mechanical interlocking technique for securing the two plies together is illustrated. In this technique, the long segment of waterproof paper 20 (FIGS. 1 and 2) consists of a long first ply of waterproof paper 70 and a long second ply of waterproof paper 72. A channel will be defined between the first and second plies of waterproof paper 70 and 72 for each of the multi-sheet segments therein. This channel will not have mechanical interlocking therein to hold the first and second plies of waterproof paper 70 and 72 together, to thereby allow the channel between the first and second plies of waterproof paper 70 and 72 to act as a passageway for liquid.

The portions of the first and second plies of waterproof paper 70 and 72 along the lateral edges have mechanical interlocking used to hold them together, which mechanical interlocking is illustrated as a series of +'s in FIG. 4. Note that in the same manner as in the first and second plies of waterproof paper 60 and 62 shown in FIG. 3, the central spaces in each multi-sheet segment of the first and second plies of waterproof paper 70 and 72 are tapered in the preferred embodiment illustrated. Thus, the mechanical interlocking is located along the lateral edges of the first and second plies of waterproof paper 70 and 72.

The first ply of waterproof paper 70 is thus mechanically interlocked onto the second ply of waterproof paper 72 to form the long segment of waterproof paper 20. Note that the entire channel formed in each multi-sheet segment between the first and second plies of waterproof paper 70 and 72 will be unobstructed throughout its length. Following this assembly operation, the perforations will be placed in the long segment of waterproof paper 20, and the long segment of waterproof paper 20 will be wound onto the cardboard tube 22.

With regard to either of the embodiments illustrated in FIGS. 3 or 4, it will be appreciated by those skilled in the art that when a multi-sheet segment of the long segment of waterproof paper 20 is removed, the multi-sheet segment will have a channel extending therethrough. The channel may be seen as a frustroconical channel which is folded flat. It will be appreciated by those skilled in the art that the frustroconical channel will act as a fluid conduit or a funnel, such that fluid admitted into the top of the frustroconical channel will pass therethrough to the bottom of the frustroconical channel.

In the preferred embodiment, the length of the frustroconical channel is approximately 27 inches in length, since the multi-sheet segment consisting of six sheets is that length. The number of sheets in the multi-sheet segment may vary between four and eight sheets, and would thus range from 18 to 36 inches.

Figure 5:
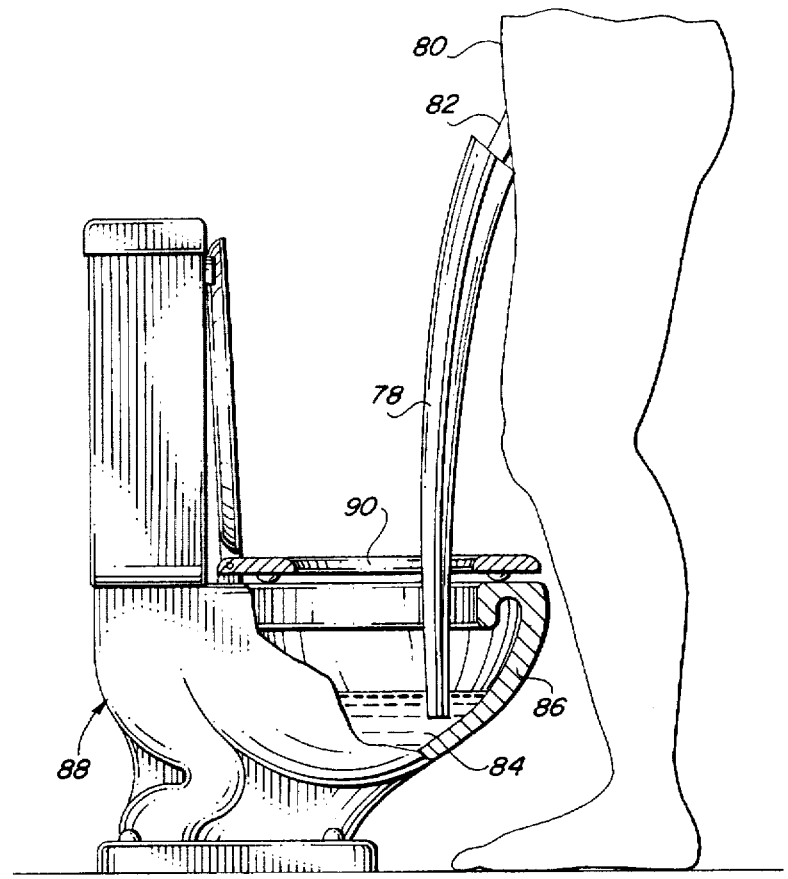
FIG. 5 is a somewhat schematic view of a man using one of the multi-sheet urinary aids of the present invention to urinate from a standing position into a toilet, showing the top end of the urinary aid fitted over the man's penis, and the bottom end of the urinary aid located in water contained in the bowl of the toilet.

Referring finally to FIG. 5, a multi-sheet segment urinary aid 78 is shown in use. The multi-sheet segment urinary aid 78 would of course first have been torn off of the roll illustrated in FIGS. 1 and 2. A man 80 places the top end of the multi-sheet segment urinary aid 78 over his penis 82. The bottom end of the multi-sheet segment urinary aid 78 is placed into water 84 in a bowl 86 of a toilet 88. Note that the seat 90 is in its lowered position.

The multi-sheet segment urinary aid 78 fits through the seat 90 into the bowl 86 of the toilet 88, where the bottom end of the multi-sheet segment urinary aid 78 rests in the water 84. The man 80 urinates, with the urine flowing through the multi-sheet segment urinary aid 78 and into the water 84 in the bowl 86 of the toilet 88.

During urination, there is virtually no sound, since the urine flows down the multi-sheet segment urinary aid 78 and into the water 84 rather than splashing down into the water 84. Note also that the seat 90 of the toilet 88 does not get wet during urination. When the man 80 is done urinating, he removes the top end of the multi-sheet segment urinary aid 78 from his penis 82. The man 80 then drops the multi-sheet segment urinary aid 78 through the seat 90 of the toilet 88 into the water 84, and flushes the toilet 88.

It may therefore be appreciated from the above detailed description of the preferred embodiment of the present invention that it teaches an improved urinary aid for facilitating the urination by men from a standing position into a toilet, which improved urinary aid may be easily and conveniently dispensed in a rest room. The improved urinary aid is deployable from a paper roll located in the toilet paper dispenser of a rest room, thereby not requiring the addition of any dispensers in rest rooms. The paper roll thus functions both as conventional toilet paper, and as a urinary aid. A method for manufacturing the improved urinary aid of the present invention is also provided by the present invention.

The urinary aid of the present invention acts as a conduit for urine from the man's penis into the water of the toilet bowl to preclude a misdirected stream of urine, thereby ensuring both quiet urination and that the toilet will remain clean even when in its lowered position. The urinary aid of the present invention fits directly onto the penis, and thereby compensates for those men who otherwise have difficulty in aiming accurately and directing urine into the water in the toilet bowl in an accurate manner. The urinary aid of the present invention is temporarily waterproof while in use, but is disposable (and biodegradeable) and may be dropped into the toilet and flushed following its use.

The urinary aid of the present invention is convenient to use, and a roll containing a plurality of the urinary aids may be easily and quickly deployed in the toilet paper holder of a rest room without requiring undue effort. The urinary aids of the present invention are of inexpensive manufacture, thereby making them eminently affordable and providing them with the broadest possible market. Finally, all of the aforesaid advantages and objectives of the urinary aid of the present invention are achieved without incurring any substantial relative disadvantage.

Although an exemplary embodiment of the present invention has been shown and described with reference to particular embodiments and applications thereof, it will be apparent to those having ordinary skill in the art that a number of changes, modifications, or alterations to the invention as described herein may be made, none of which depart from the spirit or scope of the present invention. All such changes, modifications, and alterations should therefore be seen as being within the scope of the present invention.

What is claimed is:

1. A disposable male urinary aid dispensable from a roll containing a plurality of the same thereon, comprising:
   an extended segment of two-ply paper material made from first and second plies of paper material connected to each other, said two-ply paper material being wound onto an outer side of a cylindrical tube member;
   first means for separating said extended segment of two-ply paper material into a plurality of first segments; and
   second means which, together with said first means, separates said extended segment of two-ply paper material into a plurality of sheets, said first segments each comprising multi-sheet segments;
   whereby each of said first segments of two-ply paper material defines a channel extending longitudinally therethrough between said first and second plies of paper material, said channel having an inlet end thereof and an outlet end thereof and comprising a passageway for liquid for passing liquid from said inlet end, through said channel, and out of said outlet end, each of said first segments of two-ply paper material comprising a disposable male urinary aid, said inlet end of said channel being configured to receive the penis of a male user of said urinary aid therein.

2. A disposable male urinary aid as defined in claim 1, wherein said paper material comprises:
   coated paper, wherein the coating is water impermeable for at least a short period of time, but will ultimately dissolve in water over a longer period of time.

3. A disposable male urinary aid as defined in claim 1, wherein said first and second means comprise:
   a plurality of laterally extending rows of perforations which divide said extended segment of two-ply material into said plurality of sheets.

4. A disposable male urinary aid as defined in claim 3, wherein said first means comprises:
   a plurality of laterally extending double rows of perforations which divide said extended segment of two-ply material into said plurality of first segments and thereby divide said extended segment of two-ply material into a plurality of disposable male urinary aids.

5. A disposable male urinary aid as defined in claim 4, wherein said second means comprises:
   a plurality of laterally extending single rows of perforations which, together with said plurality of laterally extending double rows of perforations, divide said extended segment of two-ply material into said plurality of sheets.

6. A disposable male urinary aid as defined in claim 1, additionally comprising:
   means for connecting said first and second plies of paper material to each other along the lateral sides of said extended segment of two-ply paper material, said connecting means being arranged and configured to maintain said channel intermediate said first and second plies of paper material.

7. A disposable male urinary aid as defined in claim 6, wherein said connecting means comprises:
   adhesive means for securing portions of said first and second plies of paper material together adjacent lateral sides of said extended segment of two-ply paper material.

8. A disposable male urinary aid as defined in claim 6, wherein said connecting means comprises:
   mechanical interlocking means for securing portions of said first and second plies of paper material together adjacent lateral sides of said extended segment of two-ply paper material.

9. A disposable male urinary aid as defined in claim 1, wherein said channel in each of said first segments of two-ply paper material is tapered from a larger size at said inlet end thereof to a smaller size at said outlet end thereof.

10. A disposable male urinary aid as defined in claim 1, wherein said extended segment of two-ply paper material and said cylindrical tube member are each approximately 4.5 inches wide.

11. A disposable male urinary aid as defined in claim 1, wherein said cylindrical tube member is of a size and is arranged and configured to fit into a standard toilet paper dispenser.

12. A disposable male urinary aid as defined in claim 1, wherein said first segments of two-ply paper material each comprise:
   between four and eight adjacent sheets of said extended segment of two-ply paper material.

13. A disposable male urinary aid as defined in claim 12, wherein said first segments of two-ply paper material each comprise:
   six adjacent sheets of said extended segment of two-ply paper material.

14. A disposable male urinary aid as defined in claim 1, wherein the length of each of said first segments of two-ply paper material ranges from approximately 18 to 36 inches.

15. A disposable male urinary aid as defined in claim 14, wherein the length of each of said first segments of two-ply paper material is approximately 27 inches.

16. A disposable male urinary aid as defined in claim 1, wherein said two-ply paper material is made from a material which is an acceptable substitute for conventional toilet paper.

17. A disposable male urinary aid as defined in claim 1, wherein said cylindrical tube member comprises:
   a cardboard tube.

18. A disposable male urinary aid dispensable from a roll containing a plurality of the same thereon, comprising:

an extended segment of two-ply paper material made from first and second plies of paper material connected to each other, said two-ply paper material being wound onto an outer side of a cylindrical tube member;

a plurality of laterally extending double rows of perforations for separating said extended segment of two-ply paper material into a plurality of first segments;

a plurality of laterally extending single rows of perforations which, together with said plurality of laterally extending double rows of perforations, separate said extended segment of two-ply paper material into a plurality of sheets, said first segments each comprising multi-sheet segments; and means for connecting said first and second plies of paper material to each other along the lateral sides of said extended segment of two-ply paper material, said connecting means cooperating with said first and second plies of paper material to define a channel extending longitudinally through each of said first segments of two-ply material between said first and second plies of paper material, said channel having an inlet end thereof and an outlet end thereof and comprising a passageway for liquid for passing liquid from said inlet end, through said channel, and out of said outlet end, each of said first segments of two-ply paper material comprising a disposable male urinary aid, said inlet end of said channel being configured to receive the penis of a male user of said urinary aid therein.

19. A method of making disposable male urinary aids dispensable from a roll containing a plurality of the same thereon, said method comprising:

winding an extended segment of two-ply paper material onto an outer side of a cylindrical tube member, said two-ply paper material being made from first and second plies of paper material connected to each other;

separating said extended segment of two-ply paper material into a plurality of first segments with a plurality of double rows of perforations;

separating said plurality of first segments into a plurality of sheets with a plurality of single rows of perforations, said first segments each comprising multi-sheet segments;

whereby each of said first segments of two-ply paper material defines a channel extending longitudinally therethrough between said first and second plies of paper material, said channel having an inlet end thereof and an outlet end thereof and comprising a passageway for liquid for passing liquid from said inlet end, through said channel, and out of said outlet end, each of said first segments of two-ply paper material comprising a disposable male urinary aid, said inlet end of said channel being configured to receive the penis of a male user of said urinary aid therein.

\* \* \* \* \*